US00PP23800P2

(12) United States Plant Patent
Gray

(10) Patent No.: US PP23,800 P2
(45) Date of Patent: Aug. 6, 2013

(54) ***HYDRANGEA* PLANT NAMED 'DANCING BUTTERFLIES TWO'**

(50) Latin Name: *Hydrangea macrophylla*
Varietal Denomination: Dancing Butterflies Two

(76) Inventor: Joseph Gray, Davis, CA (US)

( * ) Notice: Subject to any disclaimer, the term of this patent is extended or adjusted under 35 U.S.C. 154(b) by 126 days.

(21) Appl. No.: 13/317,953

(22) Filed: Nov. 1, 2011

(51) Int. Cl.
*A01H 5/00* (2006.01)

(52) U.S. Cl.
USPC ..... Plt./250

(58) Field of Classification Search
USPC ..... Plt./250
See application file for complete search history.

*Primary Examiner* — June Hwu
(74) *Attorney, Agent, or Firm* — Penny J. Aguirre

(57) ABSTRACT

A new cultivar of *Hydrangea macrophylla* named 'Dancing Butterflies Two' that is characterized by its remontant (re-blooming) habit, blooming from May until frost, its lacecap type inflorescences with single sterile flowers surrounding a mass of fertile flowers, its flowers that are light pink in color in color when grown with a soil PH of 7 or above, its sterile flowers with sepals that have a white margin on the sepals, and its cutting rooting rate that is at least 95%.

1 Drawing Sheet

Botanical classification: *Hydrangea macrophylla.*
Varietal denomination: 'Dancing Butterflies Two'.

CROSS REFERENCE TO A RELATED APPLICATION

This application is co-pending with a U.S. Plant Patent Application filed 'Cotton Candy Two' (U.S. Plant patent application Ser. No. 13/317,951).

BACKGROUND OF THE INVENTION

The present invention relates to a new and distinct cultivar of *Hydrangea macrophylla* and will be referred to hereafter by its cultivar name, 'Dancing Butterflies Two'. 'Dancing Butterflies Improved' represents a new lacecap type *Hydrangea*, a deciduous shrub grown for landscape use and for use as a potted plant.

'Dancing Butterflies Two' originated as a seedling that arose from seed planted from open pollination of *Hydrangea macrophylla* 'Frau Reiko' (U.S. Plant Pat. No. 9,500) in Davis, Calif. The male parent is unknown. The open pollination occurred in May 2005 and the new *Hydrangea* was selected as a unique single plant in June 2008.

Asexual reproduction of the new cultivar was first accomplished by the Inventor using softwood stem cuttings in Davis, Calif. in June 2008. The characteristics of this cultivar have been determined to be stable and are reproduced true to type in successive generations.

SUMMARY OF THE INVENTION

The following traits have been repeatedly observed and represent the characteristics of the new cultivar. These attributes in combination distinguish 'Dancing Butterflies Two' as a unique cultivar of *Hydrangea macrophylla.*

1. 'Dancing Butterflies Two' exhibits a remontant (re-blooming) habit, blooming from May until frost.
2. 'Dancing Butterflies Two' exhibits lacecap type inflorescences with single sterile flowers surrounding a mass of fertile flowers.

3. 'Dancing Butterflies Two' exhibits flowers that are light pink in color in color when grown with a soil PH of 7 or above.
4. 'Dancing Butterflies Two' exhibits sterile flowers with sepals that have white margins.
5. 'Dancing Butterflies Two' exhibits at least a 95% cutting rooting rate.

'Dancing Butterflies Two' differs from its female parent, 'Frau Reiko' in having a remontant blooming habit, in having a more compact plant habit, in having a much greater rooting rate, and in having 30% more branching. 'Dancing Butterflies Two' can be most closely compared to the cultivars 'Dancing Butterflies' (not patented) and 'Cotton Candy Two'. 'Dancing Butterflies' differs from 'Dancing Butterflies Two' in being more compact and in having an improved rooting rate. 'Cotton Candy Two' differs from 'Dancing Butterflies Two' in having flowers that are darker pink in color and in having a thinner white margin on the sepals of the sterile flowers.

BRIEF DESCRIPTION OF THE DRAWINGS

The accompanying colored photograph illustrates the overall appearance and distinct characteristics of the new *Hydrangea* as grown in a greenhouse in Abbotsford, British Columbia. The photographs were taken of a one year-old plant of 'Dancing Butterflies Two' as grown in a 23-cm container with a soil pH of 7. The photograph in FIG. 1 provides a close-up view of inflorescences of 'Dancing Butterflies Two'. The colors in the photographs may differ slightly from the color values cited in the detailed botanical description, which accurately describe the colors of the new *Hydrangea.*

BOTANICAL DESCRIPTION OF THE PLANT

The following is a detailed description of one year-old plants of 'Dancing Butterflies Two' grown in a greenhouse in 23-cm containers in Abbotsford, British Columbia. The detailed flower color data was taken from plants growing both under acidic conditions (with aluminum) and alkaline conditions (without aluminum) when differences exist. Phenotypic differences may be observed with variations in environmental, climatic, and cultural conditions. The color determination is in accordance with The 2001 R.H.S. Colour Chart of The Royal Horticultural Society, London, England, except where general color terms of ordinary dictionary significance are used.

General description:

*Blooming period*.—Re-blooming from May until frost from in Abbotsford, British Columbia, blooming will continue in winter with extended daylight of 18 hours.

*Plant type*.—Deciduous shrub, lacecap type Hydrangea.

*Plant habit*.—Compact mound.

*Height and spread*.—Reaches about 30 cm in height and 55 cm in width in a 23-cm container, up to 60 cm in height and width in a 3-gallon container.

*Hardiness*.—At least in U.S.D.A. Zones to 9.

*Diseases resistance*.—Has been observed to be moderately tolerant to mildew under the conditions grown.

*Root description*.—Fine.

Growth and propagation:

*Propagation*.—Softwood stem cuttings.

*Growth rate and vigor*.—Moderate to vigorous.

Stem description:

*Stem shape*.—Round, solid.

*Stem strength*.—Strong.

*Stem color*.—New growth; 145C, mature growth; 198C.

*Stem size*.—Average of 25 cm in length (excluding inflorescence), average of 5 mm in diameter.

*Stem surface*.—Glabrous and glossy.

*Internode length*.—Average of 9 cm.

*Branching*.—Average of 10 lateral branches, heavy branching habit, one pinch needed at the linear stage prior to potting into finished container.

Foliage description:

*Leaf shape*.—Broadly oval.

*Leaf arrangement*.—Opposite.

*Leaf division*.—Simple.

*Leaf number*.—Average of 12 (6 pairs).

*Leaf base*.—Cuneate.

*Leaf apex*.—Acuminate.

*Leaf margins*.—Serrate.

*Leaf venation*.—Pinnate, upper surface and lower surface; 139C in color.

*Leaf size*.—Matures to an average of 15.5 cm in length and 9 cm in width.

*Leaf attachment*.—Petiolate.

*Leaf surface*.—Smooth and dull.

*Leaf color*.—Young foliage upper and lower surface; 144D, mature foliage upper surface; 147B, mature foliage lower surface; 137B.

*Petioles*.—Average of 3 cm in length and 5 mm in diameter, 140C in color, glabrous surface.

Inflorescence description:

*Inflorescence type*.—Terminal compound corymb, lacecap in form comprised of a center region of fertile flowers surrounded by an outer ring of single sterile flowers.

*Lastingness of inflorescence*.—Persistent but color is retained for about 4 weeks.

*Inflorescence number*.—One per lateral or sublateral stem if pinched.

*Inflorescence size*.—Average of 10.5 cm in depth and 20 cm in width.

*Flower number*.—Average of 10 sterile flowers and 190 fertile flowers per panicle.

*Flower fragrance*.—None.

*Flower aspect*.—Upright and outward.

*Flower size*.—Sterile flowers; average of 4 cm in diameter and 1 cm in depth, fertile flowers; average of 3 mm in diameter and 1 cm in depth.

*Flower type*.—Rotate.

*Flower buds*.—Sterile flowers; average of 6 mm in length and 4.5 mm in width prior to opening, ovate in shape, 62A in color, fertile flowers; average of 4 mm in width and diameter, obovate to rounded in shape, 62A in color.

*Peduncles*.—Moderately strong, average of 5 cm in length and 4 mm in width, average angle of 10° from vertical, 66B in color.

*Pedicels*.—Held at a 20° angle from vertical, average of 2 cm in length and 2 mm in width on sterile flowers and an average of 4 mm in length and 1 mm in width on fertile flowers, 66B in color and glabrous surface on all flowers.

*Petals*.—Fertile flowers; average of 5, rotate in arrangement, ovate to lanceolate in shape, serrated margin, rounded apex, truncate base, average of 4 mm in length and 2 mm in width, surface is smooth and dull on both surfaces, color of upper and lower surface is 66B with thin margin (<1 mm) of 155A and fading to 67D, sterile flowers; an average of 4 comprised the eye, eye is an average of 2 mm in diameter and depth, 69D in color on mature flowers, glabrous surface.

*Sepals*.—Sterile flowers; average of 4, ovate to broadly ovate in shape, an average of 2 cm in length and width, broadly acute apex, cuneate to rounded base, glabrous surface on upper and lower surface, entire margins, color when grown with a soil pH of 7 color when flower opens upper and lower surface; 155A with and flushed in center with 75C, color when flower is fully open upper and lower surface; 75A with a wide margin of a color whiter than 155A, fertile flowers; 6, ovate to lanceolate in shape, serrated margin, obtuse and refuse apex, attenuate base, average of 3 mm in length and 2 mm in width, surface is smooth and slightly glossy on both surfaces, color of upper and lower surface on open flower is 67A.

Reproductive organs: (fertile flowers).

*Stamens*.—Average of 15, anther is oblong in shape, 1 mm in length and 80B in color, filament is 5 mm in length, pollen is scarce in quantity and 200D in color.

*Pistils*.—Average of 4, average of 1 mm in length, stigma is rounded and 79A in color, style is an average of 1 mm in length and 79A in color, ovary is 145B in color.

*Fruit and seed*.—Has not been observed under the conditions tested to date.

It is claimed:

1. A new and distinct cultivar of *Hydrangea* plant named 'Dancing Butterflies Two' substantially as herein illustrated and described.

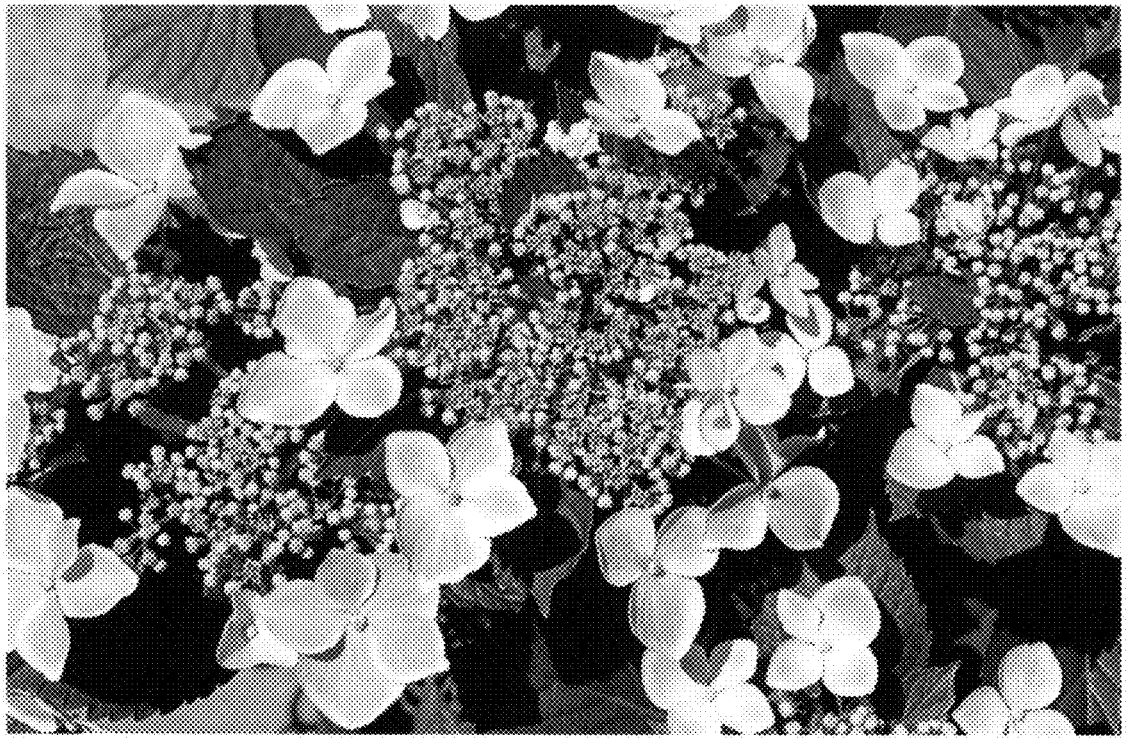

* * * * *